United States Patent [19]

Sundrehagen

[11] Patent Number: 6,103,478
[45] Date of Patent: Aug. 15, 2000

[54] CDT ASSAY

[75] Inventor: Erling Sundrehagen, Oslo, Norway

[73] Assignee: Axis-Shield ASA, Oslo, Norway

[21] Appl. No.: 09/026,156

[22] Filed: Feb. 19, 1998

Related U.S. Application Data

[60] Division of application No. 08/716,913, Sep. 9, 1996, Pat. No. 5,798,212, which is a continuation-in-part of application No. PCT/GB96/00395, Feb. 21, 1996.

[30] Foreign Application Priority Data

Feb. 22, 1995 [GB] United Kingdom ............... 9503484
Mar. 24, 1995 [GB] United Kingdom ............... 9506045
Aug. 17, 1995 [GB] United Kingdom ............... 9516885

[51] Int. Cl.[7] ............................................. G01N 33/53
[52] U.S. Cl. .................. 435/7.1; 435/287.1; 435/287.2; 435/810; 435/962; 435/973; 435/975; 436/161; 436/177; 436/178; 436/512; 436/514; 436/518; 436/524; 436/528; 436/529; 436/531; 436/534; 436/808
[58] Field of Search ................. 435/7.1, 287.1, 435/287.2, 810, 962, 973, 975; 436/161, 177, 178, 512, 514, 518, 524, 528, 529, 531, 534, 808

[56] References Cited

U.S. PATENT DOCUMENTS 4,626,335  12/1986  Joustra et al. ........................ 210/635
5,798,212  8/1998  Sundrehagan ........................ 435/7.1

FOREIGN PATENT DOCUMENTS

0333939 A2  9/1989  European Pat. Off. .
0333939 A3  9/1989  European Pat. Off. .
62239056  10/1987  Japan .
WO 85/03578  8/1985  WIPO .
WO 91/19983  12/1991  WIPO .
WO 95/04932  2/1995  WIPO .

OTHER PUBLICATIONS

Int. J. Peptide Protein Res. 10, 1977, 17–26.
Anaesthesist, (1994) 43:447–453.
Advances in the Biosciences 71, 1988, 353–357.
Clinica Chimica Acta, 132 (1983) 167–171.
Int. J. Peptide Protein Res. 9, 1977, 241–248.
Beckman, Rate Nephelemetric Determination of Carbohydrate Deficient Transferrin.

*Primary Examiner*—Christopher L. Chin
*Attorney, Agent, or Firm*—Alston & Bird LLP; Karen Lee Orzechowski

[57] ABSTRACT

The invention provides a method of assessment of carbohydrate-deficient transferrin in a transferrin containing body fluid, said method comprising the steps of:

i) obtaining a transferrin containing liquid sample of or derived from a said fluid;

ii) contacting said sample with a source of iron ions;

iii) subsequently contacting said sample with an anionic ion exchange resin at a pH such as to cause carbohydrate-deficient transferrin to be retained by said resin;

iv) subsequently contacting said resin with an eluant serving to release carbohydrate-deficient transferrin into the eluate from said resin;

v) collecting a volume of said eluate substantially free from tetra- and penta-sialo transferrin; and vi) assessing the transferrin variant content in said volume of eluate.

By including at least a proportion of the trisialotransferrin in the eluate, it is possible to use relatively simple assessment techniques such as turbidimetry in the assay.

23 Claims, 4 Drawing Sheets

NA: TOTAL ABSTAINERS
SD: SOCIAL DRINKERS
A: ADMITTED FOR ALCOHOLISM TO HOSPITAL r = 0.95
slope = 1.01
n = 18

CDT ASSAY

RELATED APPLICATIONS

This application is a divisional of U.S. Ser. No. 08/716,913, filed on Sep. 9, 1996, now issued as U.S. Pat. No. 5,798,212, which is a continuation-in-part of the US designation of International Patent Application No. PCT/GB96/00395, filed Feb. 21, 1996.

FIELD OF THE INVENTION

This invention relates to an assay method for assessing carbohydrate-deficient transferrin (CDT), and to kits and apparatus for performing the assay.

BACKGROUND OF THE INVENTION

Serum transferrin is a glycoprotein with a molecular weight of about 80 kD which comprises a single polypeptide chain with two N-linked polysaccharide chains. These polysaccharide chains are branched and terminate in five antennae with terminal sialic acid residues.

Wong and Regoeczi, in Int. J. Peptide Res. 9:241–248 (1977), reported that human transferrin was naturally heterogeneous, occurring in variant forms with different levels of sialylation. In fact there appear to be six such variants, the pentasialo, tetrasialo, trisialo, disialo, monosialo and asialo transferrins.

In the normal healthy individual, the tetrasialo variant appears to predominate; however it has been found that the asialo, monosialo, disialo and, to some degree the trisialo variants occur in elevated levels in the blood of alcoholics (see van Eijk et al in Clin Chim Acta 132:167–171(1983), Stibler in Chin Chim 37:2029–2037(1991) and Stibler et al in "Carbohydrate-deficient transferrin (CDT) in serum as a marker of high alcohol consumption", Advances in the Biosciences, (Ed Nordmann et al), Pergamon, 1988, Vol. 71, pages 353–357).

The asialo, monosialo, disialo and trisialo variants are referred to herein as carbohydrate-deficient transferrin or CDT.

CDT has been found to be an effective marker for alcohol consumption, in particular for detecting and monitoring chronic alcohol consumption, and unlike conventional tests (e.g. GGT or MCV) can be used to screen for heavy alcohol intake in patients with liver disease.

As a result, several diagnostic assays for CDT have been described in patent and scientific literature.

In U.S. Pat. No. 4,626,355 (Joustra), Pharmacia AB describes a chromatographic assay in which a dilute serum sample is passed over an anionic ion exchange column with the pH and ion content of column and sample balanced to permit asialo, monosialo and disialo CDTs to eluate through in an isocratic procedure while the trisialo and the "normal" tetra and pentasialo variants are retained on the column. The CDT content of the eluate is then determined by competitive immobilization of CDT and radiolabelled-transferrin on an antibody carrying solid phase.

In a recent poster entitled "Rate nephelemetric determination of carbohydrate-deficient transferrin", Schellenberg, Martin, Bénard, Circaud and Weill of Laboratoire de Biochimie CHU Trouseau, Tours, Centre Louis Sevestre, La Membrolle sur Choisille and Beckman France, Gagny, France described a similar isocratic chromatographic separation in which dilute serum is passed through an anionic ion exchange column causing the normal transferrin variants to be retained and allowing CDT to elute through. The eluate is then mixed with polyethyleneglycol and centrifuged, an anti-transferrin antibody is added to the supernatant and the CDT content is assessed by nephelometry.

Heil et al, in Anaesthetist 43:447–453(1994) have reported a further isocratic chromatographic procedure for CDT determination. In their procedure a dilute serum sample is passed through an anionic ion exchange resin, again causing normal transferrin variants to be retained while permitting transit of CDT. The CDT content of the eluate is determined by latex particle enhancement of CDT concentration in an immunoturbidimetric assay procedure.

In WO-91/19983 (Sundrehagen), Axis Research AS described an alternative CDT assay in which a dilute serum sample (in which the transferrin variants are bound by labelled (e.g. fluorophore-labelled) antibodies or antibody fragments reactive with all variants) is passed through an anionic ion exchange resin and the label concentration in the eluate is determined (e.g. by fluorescence measurement) as a function of eluate fraction. This assay relies upon the elution rates being different for the different variant:labelled binding partner complexes.

All of the assay procedures mentioned above rely upon relatively complex procedures which are not directly applicable to many of the automated multi-task diagnostic machines commonly used by diagnostic laboratories.

SUMMARY OF THE INVENTION

We have now found that CDT may be assessed in a straightforward fashion which permits simple measurement techniques such as turbidimetry to be used without needing signal amplification steps such as required by the procedure of Heil et al (supra).

Thus, viewed from one aspect the invention provides a method of assessment of carbohydrate-deficient transferrin in a transferrin containing body fluid, said method comprising the steps of:

i) obtaining a transferrin containing liquid sample of or derived from a said fluid;

ii) contacting said sample with a source of iron ions;

iii) subsequently contacting said sample with an anionic ion exchange resin at a pH such as to cause carbohydrate-deficient transferrin to be retained by said resin;

iv) subsequently contacting said resin with an eluant serving to release carbohydrate-deficient transferrin into the eluate from said resin;

v) collecting a volume of said eluate substantially free from tetra- and pentasialo transferrin; and vi) assessing (eg. determining a quantitative value for the concentration or relative concentration or providing an indication as to whether the concentration or relative concentration falls above or below a preselected threshold, eg. one indicative of alcohol misuse) the transferrin variant content in said volume of eluate.

The body fluid used in the assay of the invention may be any transferrin-containing fluid such as synovial fluid or amniotic fluid; however for investigation of alcohol consumption or abuse the fluid will generally be blood. Where this is the case, the liquid sample will preferably be cell-free. Either serum or plasma, i.e. blood derived transferrin containing fluids, are preferred.

Viewed from a further aspect, the invention provides a kit for a diagnostic assay according to the invention, said kit comprising:

an iron ion containing buffered incubation solution having a pH of at least 6.2, preferably about 7.0;

preferably, a transferrin solution of known concentration and more preferably a set of such solutions having a range of transferrin concentrations;

an anionic ion exchange resin packed in a container having sample introduction and eluate removal ports;

preferably, a flushing eluant having a pH and ionic strength insufficient to release transferrin from said resin;

a release eluant having a pH and ionic strength sufficient to release transferrin from said resin;

preferably, a light transmitting eluate receiving vessel;

preferably, an anti-transferrin antibody or antibody fragment; and preferably, an opacification enhancer.

One particular preferred kit comprises simply the incubation solution, the resin (in its container), the flushing eluant and the release eluant.

If desired an automated apparatus may be arranged to receive a transferrin containing body fluid sample, incubate it with an iron-containing incubation solution, apply the incubated solution to an anionic ion exchange resin, optionally flush the resin, apply a release eluant, collect a CDT containing eluate, apply an opacifying anti-transferrin antibody or antibody fragment, and determine CDT content in the eluate. Such apparatus is also deemed to fall within the scope of the invention.

BRIEF DESCRIPTION OF THE ACCOMPANYING DRAWINGS

FIG. 1 is a typical turbidimetric calibration curve showing absorption at 405 nm as a function of transferrin content;

FIGS. 2, 3 and 5 are graphical presentations of test results in terms of % CDT for non-alcoholics or total abstainers (NA or TA), social drinkers (SD), alcoholics (AL) and pregnant women (PW), in these figures 0-2-s Trf or 2 sialo indicates that the assessed CDT included the asialo, monosialo and disialo variants, 0-3-s Trf or 2 sialo +100% 3-s indicates that the assessed CDT also included the trisialo variant;

DETAILED DESCRIPTION OF THE INVENTION

Figure 1:
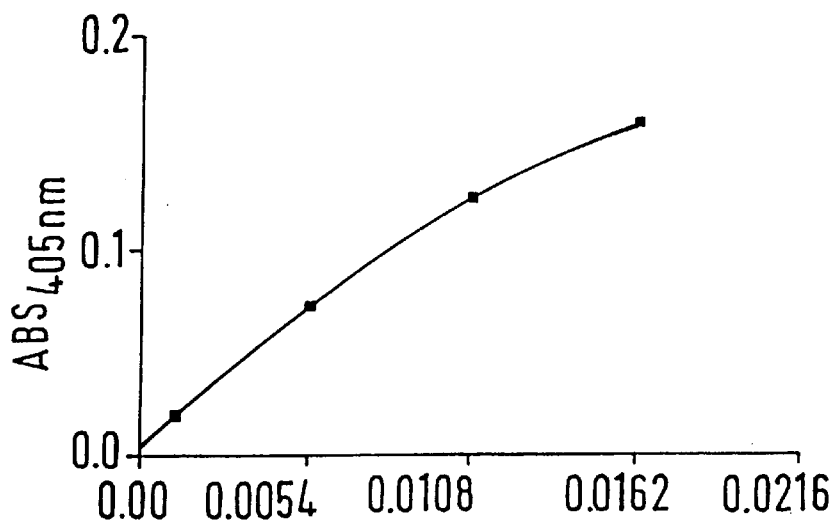

The chromatographic technique of the invention operates effectively where the transferrin variants are iron ion-loaded and before application to the resin the liquid sample will be contacted with a source of iron ions, e.g. an aqueous Fe(III) solution or a finely divided soluble iron salt. In general, it is desirable although not essential to avoid unnecessary dilution of the sample at this stage. The iron treatment of the sample may simultaneously be used to set the pH of the sample at a level sufficiently high as to cause the CDT variants to be retained by the ion exchange resin. Even though high concentrations of competing anions, such as the plasma chloride ions, can serve to reduce resin immobilization of the transferrins, at sufficiently high pH it is found that the CDTs are nonetheless retained by the resin. The particular pH used will depend upon the nature of the resin, the dilution of the sample, and the competing anion content of the sample (or the resin before sample loading). However in general a pH of at least 6.2, preferably 6.5 to 10, and especially 6.8 to 7.5, e.g. about 7.0, will be used. Thus in effect the pH and the ionic strength together will be such as to cause the CDTs to be retained by the resin.

In a preferred aspect, a blood sample of 10 $\mu$L to 2.5 mL will be used to provide a plasma or serum sample if 4 $\mu$L to 1 mL, preferably 50 to 500 $\mu$L, especially about 100 to 200 $\mu$L, which is incubated with an iron containing, relatively low competing anion content buffer, e.g. of pH 7.0. At this stage, there is a dilution of up to 1:8, preferably 1:1 to 1:5, especially about 1:2, by volume by the iron-containing buffer solution.

Besides buffering agents such as Tris (tris(hydroxymethyl)aminomethane) and Bis-Tris (bis(2-hydroxyethyl)amino-tris(hydroxymethyl)methane) and iron ion sources (such as $FeCl_3$), the buffer solution may contain acids such as HCl to set the pH and iron stabilizers such as citrate and maleate. However the concentration of competing anions such as chloride (or cyanide, sulphate etc) should be kept low and iron salts of such anions should not be used in great excess beyond that required to iron-load the transferrins.

The sample, incubated for some minutes with the iron source, e.g. 2 to 30 minutes, preferably 5 to 10 minutes, is then applied to the ion exchange resin.

For this purpose any anionic ion exchange resin which is in charged form may be used. Suitable such materials are the tertiary and quaternary amine resins and in particular materials such as PBE94, DEAE-Sepharose or Q-Sepharose obtainable from Pharmacia AB of Sweden or Poros 50 HQ obtainable from Perseptive Inc, USA. Fast flow Q-Sepharose is especially preferred as it is positively charged over a wide pH range.

The resin will generally be in uniformly packed columns, e.g. filled with a given resin volume, allowed to settle and then tamped down with a low pressure. Above the resin there will preferably be a porous element, such as an inert nylon or polyethylene mesh, filter or frit, which keeps the resin in place and which by virtue of capillary forces serves to prevent air entering the resin after sample or eluants are introduced. In this way the volume of eluate is simply controlled by the volume of eluant added and so careful control of eluant volume automatically gives control of eluate volume and, for the release eluant, thereby gives control of the percentage of any given CDT released into the eluate. Preferably the column will have the resin disposed between two porous elements, e.g. porous frits such as the Porex frits available from Porex of Atlanta, Ga., USA. In practice moreover such columns will preferably be provided pre-loaded with a low ionic strength transportation buffer, e.g. a bis-tris buffer having the same pH as the iron-containing incubation buffer discussed above.

The volume of resin used will depend on the sample volume to be applied to the resin as well as on the nature of the resin. It should be sufficient to absorb substantially all of the transferrin in the sample. With a 200 $\mu$L serum sample, 1 mL resin loaded in 5 mm diameter tubes has been found to be adequate. Preferably however 7 mm internal diameter tubes loaded with 1.24 cm resin are used.

Before the sample is applied to the resin, any transportation buffer is first allowed to drain off.

Following application of the sample to the resin any eluate is discarded. The resin is then preferably flushed with a low ionic strength eluant (i.e. one which is relatively free of anions such as chloride which compete with the transferrin variants in binding to the resin) of a pH sufficiently high as not to cause transferrin variants to be released, e.g. a Bis-Tris or Tris buffer solution of pH 6.2 or above, preferably 6.25 to 6.5. In this way, unbound material and plasma anions may be flushed from the column. For a 1 mL resin column, a flushing volume of 0.3 to 5 mL, preferably 2 mL, might conveniently be used. Again any eluate is discarded.

The resin is then contacted with an eluant (the release eluant) which serves to release the bound transferrin e.g. by virtue of its low pH and/or high content of competing anions (such as chloride, cyanide, sulphate etc), and a volume of the eluate containing the CDT variants is collected. If, as is preferred, the pH and ionic strength of the release eluant are such as to release the "normal" (tetrasialo and pentasialo) transferrins, it is important that the transferrin release be calibrated so that the collected volume is substantially free of such "normal" transferrins. This may readily be done by loading exemplary columns with tetrasialo-transferrin, collecting volume fractions of the eluate and determining at which fraction the tetrasialo variant begins to elute. The volume of release eluant used may thus be set to be the volume which causes the asialo, monosialo and disialo, and preferably also the trisialo, variants to appear in the eluate but which yields an eluate substantially free of the "normal" variants. Resin packs columns should be calibrated in this way on a production batch basis.

The release eluant is preferably administered using a calibrated micropipette to ensure the correct volume is administered. The volume administered should preferably be within 3% of the desired (ie. calibration) volume, more preferably within 1 to 2%.

The release eluant and the CDT loaded resin should preferably be at a temperature within 5C. ° of the desired (calibration) value, e.g. 25° C., and more preferably within 1C. °.

The release eluant will generally have a pH of between 5.0 and 6.8, preferably between 5.5 and 6.5, especially preferably between 5.9 and 6.3, particularly about 6.0. The pH of the release eluant should preferably be withn 0.03 pH units of the desired value. The eluant again will preferably be buffered and higher buffer contents than in the incubation and flushing eluants are generally preferred, e.g. about 50 mm Bis-Tris. The release eluant thus generates a pH gradient in the resin and causes sequential release of transferrin variants into the eluate thereby enabling the CDT fraction to be selected for calibrated columns. The competing anion content in the release eluant will depend upon the nature of the anion and the resin and also on the nature and concentration of the buffer. For a release eluant buffered with 50 mM Bis-Tris, a chloride content (as NaCl for example) of 1.5 to 25 mM, especially 3 to 15 mM, more especially 3 to 10 mM, particularly 5 to 7 mM may conveniently be used in addition to the chloride deriving from the HCl used for pH regulation. The chloride content of the release eluant should preferably be within 1 mM of the desired value.

By way of example for 1 mL Q-Sepharose columns, it has been found that 3 mL of a 50 mm Bis-Tris, 6 mM NaCl, pH 6.0 release eluant enables the CDT fractions to be isolated in the 2 mL eluate collected. Similarly, Example 5 below shows how the asialo to trisialo variants may be eluted from Poros 50 HQ into the 3 mL eluate collected.

From the foregoing, it will be clear that the degree of dilution of the CDT variants in the body fluid on passing from the body fluid sample (e.g. blood) to the collected eluate is relatively small. This is one of the important characteristics of the present invention. Thus for example, 500 $\mu$L blood may yield 200 $\mu$L serum which in due course yields 2000 $\mu$L of CDT-containing eluate. In practice, as little as 100 $\mu$L serum may be sufficient. The volume dilution from serum (or plasma) to eluate will preferably be no more than 50:1 especially preferably no more than 25:1 and particularly no more than 15:1.

The collected eluate containing the CDT variants is then assessed for CDT content. This may be done by any standard immunoassay technique, e.g. an ELISA or radio immunoassay technique. However an important advantage of the assay method of the invention is that it enables assay methods which do not require further separation steps to be used (e.g. nephelometry) and in particular that it allows turbidimetric determination of CDT content. This is important since although nephelometry is in general a more sensitive probe for the production of opacity in a fluid sample than is turbidimetry, the technique requires a non-linear optical path for the detection apparatus and thus is not readily adapted for inclusion within existing multi-task light-absorbance determination based diagnostic assay apparatus in which the light path through the sample is linear.

For either turbidimetric or nephelometric CDT determination, opacity will generally be generated by contacting the eluate with an anti-transferrin antibody or antibody fragment, e.g. a rabbit anti-human transferrin antibody such as is commercially available from Dako of Copenhagen, Denmark. The Dako antibodies are specific to transferrin and show no cross reactions with other blood proteins that may be present in the eluate. The quantity of antibody used should of course be optimised against transferrin containing standard samples as opacification arises from the hook effect whereby multiple transferrin binding generates the opacification centres.

As in routine turbidimetric and nephelometric assays, a polymeric opacification enhancer such as polyethyleneglycol is preferably also added to the eluate.

In making the determination of CDT content using such measuring techniques, a kinetic reading mode may of course be used.

Before the nephelometric or turbidimetric determination is made, the eluate, antibody and enhancer should be incubated for a short period, e.g. 5 minutes to an hour, preferably about 10 minutes.

The light used in the determination of opacification should have an appropriate wavelength. In this regard we have found that use of a 405 nm filter, or more preferably a 340 nm filter, yields particularly good results.

In general, besides the sample under evaluation, calibration samples with known transferrin contents will also be assessed in the performance of the assay method of the invention. Such determinations can be used to plot a calibration curve from which the CDT content of the sample under evaluation may be determined. Preferably calibration samples having transferrin contents of up to 0.05 mg/mL (e.g. 0.002, 0.01, 0.02 and 0.03 mg/ml) will be used. (These will not of course be passed through the resin columns to separate out the "normal" variants).

Moreover in the assay method of the invention the total transferrin content of the sample will preferably be determined, e.g. with a diluted, non-chromatographed, aliquot using the same assay procedure (i.e. turbidimetry etc).

In this way the CDT content may be determined as a percentage of total transferrin (% CDT). % CDT is a more precise marker for alcohol consumption than total CDT, with 6% representing the threshold value.

Heretofore there has been doubt as to whether or not the trisialo transferrin variant is or is not indicative of alcohol consumption or abuse. On the one hand Van Eijk et al. in their 1983 paper "The microheterogeneity of human transferrins in biological fluids" in Clin. Chim. Acta 132: 167–171 (1983) stated that "the higher concentration of disialo transferrin in alcoholics has already been reported . . . but the CIE [crossed immunoelectric focussing] methods reveal that, also tri-, mono- and asialo-transferrin bands are elevated". On the other hand, however, Pharmacia AB in their patent U.S. Pat. No. 4,626,355 (Joustra) described a technique for separating out the asialo, monosialo and disialo variants from the trisialo, tetrasialo and pentasialo variants by isocratic chromatography, acknowledging that the asialo, monosialo and disialo variants occur at elevated levels in cases where alcohol consumption has been high but stating that "the other isotransferrins, which have no clinical relevance in the context of excessive alcohol consumption, are pentasialo, tetrasialo and trisialo transferrin".

The even more recent patent application WO95/04932 of Biolin Medical similarly identified only the asialo, monosialo and disialo transferrins as markers for alcoholism.

As a result it is clear that no significant importance has previously been attached to the trisialo transferrin content in body fluids.

We have now found that the trisialo transferrin content, even in the absence of the other CDT variants is a strong indication of alcoholism and that in combination with the other CDT variants it yields a significantly clearer distinction between alcoholics and non-drinkers or social drinkers than is possible with an assay of only the asialo, monosialo and disialo variants.

By including some or all of the trisialotransferrin in the CDT fraction assessed, it is possible to use assay techniques (such as turbidimetry for example) that are simpler and more rapid to perform but inherently less precise than prior art techniques while still achieving results with as good or better confidence values.

Thus viewed from a further aspect the invention provides a method of assaying for alcohol consumption, said method comprising assessing a blood derived body fluid sample for its content of a desialo transferrin, characterised in that said desialo transferrin comprises trisialo transferrin, and optionally and preferably one or more of disialo, monosialo and asialo transferrin, particularly preferably all three.

In this method, the assessed desialo transferrin content is preferably determined as a proportion of the total transferrin content (e.g. as % CDT), with 6% being viewed as the threshold value indicative of alcoholism where the assessed desialo transferrin comprises the asialo, monosialo and disialo and 50% of the trisialo variants.

Alternatively viewed the invention provides a method of assaying for alcohol consumption, said method comprising obtaining a first transferrin containing liquid ample of or derived from a body fluid and containing tetra- and pentasialo transferrins;

obtaining from said first sample a second transferrin containing liquid sample, e.g. by elution from a column, said second sample being substantially free from tetra- and pentasialo transferrin and having a transferrin content of at least 1 mg/L, preferably at least 2 mg/L; and turbidimetrically assessing the transferrin content of said second sample.

In particular we have found that including trisialotransferrin in the assay improves discrimination between alcoholics and people with other liver diseases.

In these methods, the desialo transferrin is preferably assessed as a percentage of total transferrin in the sample although, less preferably, it may be assessed as an actual concentration (ie. a mass per unit volume). The assay technique used may be any convenient technique, but techniques as described herein or in U.S. Pat. No. 4,626,355, WO91/19983, WO95/04932, Schellenberg et al. (supra) or Heil et al (supra), the contents whereof are incorporated herein reference, are especially preferred.

In the methods of the invention, it is particularly preferred only to assess a fraction (albeit a major fraction for example from 25 to 95%, preferably 30 to 70% especially 40 to 60% and especially preferably about 50%) of the trisialotransferrin, preferably in combination with lower sialylated asialo transferrins, in particular one or more and especially all three of asialo, monosialo and disialo ransferrins.

This partial assessment of the trisialo variant may readily be achieved in the method of the invention by selecting a volume of release eluant which releases only the required fraction of the trisialo variant into the eluate. Apparatus may readily be calibrated as described herein in order to determine what release eluant volume is required to release the desired fraction of the trisialo variant.

This method in which a major fraction of the trisialo variant is assessed is particularly advantageous since it avoids potential contamination by the tetrasialo variant (since mini columns of the type described herein generally have lower resolution than HPLC) and since it makes the assay more sensitive to the lower desialylated variants which are generally significantly less abundant than the trisialo variant.

The invention will now be described in further detail with reference to the following Examples.

EXAMPLE 1

Assay Kit

Equipment

Tubes (5 mm diameter containing 1 mL Q-sepharose (Pharmacia) covered with a nylon top filter)
Pipettes covering volumes from 4 $\mu$l to 3 ml Alternatively: multipipettes for volumes 100 $\mu$l, 200 $\mu$l, 2 ml and 3 ml
Racks (for tubes 75×12 mm)
Microtiter plates
Reader for microtiter plates, 405 nm filter Reagents Solution A
 10 mM BisTris(bis(2-hydroxyethyl)amino-tris (hydroxymethyl)methane)
 1.5 mM Sodium Azide
 0.05% Tween 20
 1 M HCl ad pH 7.0
 0.4 mM Tris base (Tris(hydroxymethyl)aminomethane)
 0.075 mM $FeCl_3$
 0.075 mM Sodium Citrate
 0.2 mM Maleic acid
 deionized $H_2O$ q.s.

Solution B
  10 mM BisTris(bis(2-hydroxyethyl)amino-tris(hydroxymethyl)methane)
  3.1 mM Sodium Azide
  0.1% Tween 20
  1 M HCl ad pH 6.25
  deionized H₂O q.s.
Solution C
  50 mM BisTris(bis(2-hydroxyethyl)amino-tris(hydroxymethyl)methane)
  3.1 mM Sodium Azide
  0.05% Tween 20
  1 M HCl ad pH 6.00
  5 mM NaCl added
  deionized H₂O q.s.

Human Normal Serum

For calibration containing
  2.17 mg/ml Transferrin

Turbidimetric Reagent

900 μl 0.1 M PEG-PBS pH 8.2
  100 μl Rabbit anti-human transferrin (Dako)
The 0.1 M PEG-PBS pH 8.2 Comprises
  91.8 mM Disodiumhydrogenphosphate
  8.3 mM Sodiumdihydrogenphosphate *2H₂O
  3.1 mM Polyethylene glycol
  3.1 mM Sodium Azide
  2 M NaOH ad pH 8.2
  deionized H₂O q.s.

EXAMPLE 2

Alternative Assay Kit

Equipment

Columns (5 mm diameter containing 0.5 mL Poros 50 HQ (Perseptive Inc, USA) covered with a nylon top filter)
Pipettes covering volumes from 4 μl to 3 ml Alternatively: multipipettes for volumes 100 μl, 200 μl, 2 ml and 3 ml
Racks (for tubes 75×12 mm)
Microtiter plates
Reader for microtiter plates, 405 nm filter Reagents Solution A
  10 mM BisTris(bis(2-hydroxyethyl)amino-tris(hydroxymethyl)methane)
  1.5 mM Sodium Azide
  0.05% Tween 20
  1 M HCl ad pH 7.0
  0.4 mM Tris base (Tris(hydroxymethyl)aminomethane)
  0.15 mM FeCl₃
  0.15 mM Sodium Citrate
  0.4 mM Maleic acid
  deionized H₂O q.s.
Solution B
  10 mM BisTris(bis(2-hydroxyethyl)amino-tris(hydroxymethyl)methane)
  3.1 mM Sodium Azide
  0.1% Tween 20
  1 M HCl ad pH 6.25
  deionized H₂O q.s.
Solution C
  50 mM BisTris(bis(2-hydroxyethyl)amino-tris(hydroxymethyl)methane)
  3.1 mM Sodium Azide
  0.05% Tween 20
  1 M HCl ad pH 6.00
  15 mM NaCl added
  deionized H₂O q.s.

Human Normal Serum

For calibration containing
  2.17 mg/ml Transferrin

Turbidimetric Reagent

900 μl 0.1 M PEG-PBS pH 8.2
  100 μl Rabbit anti-human transferrin (Dako)
The 0.1 M PEG-PBS pH 8.2 Comprises
  91.8 mM Disodiumhydrogenphosphate
  8.3 mM Sodiumdihydrogenphosphate *2H₂O
  3.1 mM Polyethylene glycol
  3.1 mM Sodium Azide
  2 M NaOH ad pH 8.2
  deionized H₂O q.s.

EXAMPLE 3

Preparation of Calibrators and Columns

Prepare 4 calibrators using human normal serum. See table 1 for dilutions

TABLE 1

Preparation of calibrators:

| Calibrators (mg/ml) | Human normal serum containing 2.17 mg transferrin/ml | Solution C |
|---|---|---|
| C1:0.002 | 100 μl C3 | 900.0 μl |
| C2:0.01 | 4.6 μl | 995.4 μl |
| C3:0.02 | 10.1 μl | 1089.9 μl |
| C4:0.03 | 13.8 μl | 986.2 μl |

(Calibrator C1 is produced by dilution of calibrator C3 with Solution C of Example 1 or Example 2).

Preparation of Columns

Use one column for each sample to be tested. Elute surplus transport buffer by removing first the top and thereafter the bottom stopper, discard the eluate. Prepared columns should be used within 2 hours.

EXAMPLE 4

Sample Testing Procedure

Sample Procedure
  1. Add 200 μl serum to 400 μl solution A (of Example 1) in a test tube. Mix.
  2. Incubate for 5–10 minutes at ambient temperature.
Column Separation
  1. All solutions added must elute freely from the column.

2. Add 500 μl incubated sample to a column.
3. Let the sample sink into the top filter before adding 2.0 ml of solution B.
4. Let solution B sink into the top filter. Change tubes below columns. Solution eluted up to this point should be discarded. Add 3 ml of solution C (of Example 1) to each column. Collect 2 ml eluate C.

Measurement

1. Add 100 μl of each calibrator, and 100 μl of eluate C from the column separation to separate wells of a microtiter plate.
2. Add 100 μl turbidimetric reagent to each well.
3. Incubate for 10 minutes at ambient temperature.
4. Read results using a reader with 405 nm filter.
5. Establish a calibration curve using non-linear regression. FIG. 1 shows a typical calibration curve.
6. CDT in the serum sample is calculated from the calibration curve.

EXAMPLE 5

Sample Testing Procedure

Sample Procedure

1. Add 100 μl serum to 200 μl solution A (of Example 2) in a test tube. Mix.
2. Incubate for 5–10 minutes at ambient temperature.

Column Separation

1. All solutions added must elute freely from the column.
2. Add 200 μl incubated sample to a column.
3. Let the sample sink into the top filter before adding 1.0 ml of solution B.
4. Let solution B sink into the top filter. Change tubes below columns. Solution eluted up to this point should be discarded. Add 3 ml of solution C (of Example 2) to each column. Collect 3 ml eluate C.

Measurement

1. Add 100 μl of each calibrator, and 100 μl of eluate C from the column separation to separate wells of a microtiter plate.
2. Add 100 μl turbidimetric reagent to each well.
3. Incubate for 10 minutes at ambient temperature.
4. Read results using a reader with 405 nm filter.
5. Establish a calibration curve using non-linear regression. FIG. 1 shows a typical calibration curve.
6. CDT in the serum sample is calculated from the calibration curve.

EXAMPLE 6

Figure 2:
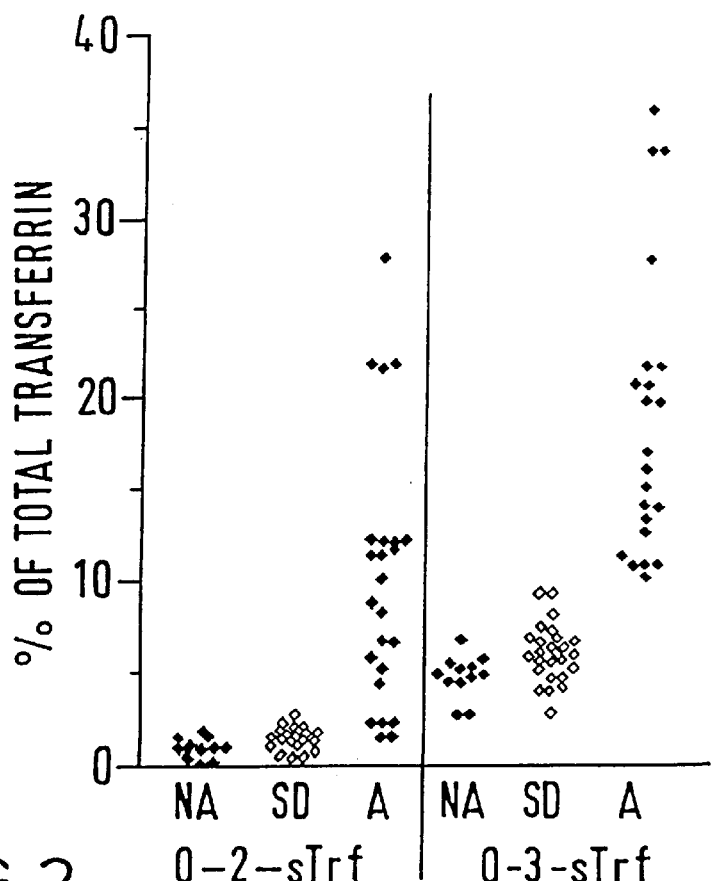

Comparison of Assaying for Asialo, Monosialo and Disialo Transferrin as Against for Asialo, Monosialo, Disialo and Trisialo Transferrin Serum samples from three test groups were analysed for asialo, monosialo, disialo and trisialo transferrin using the HPLC technique described in WO 95/04932. The results presented in Table 2 below and in FIG. 2 show asialo+ monosialo+disialo (0–2 sTr) and asialo+monosialo+disialo+ trisialo (0–3 sTr) contents as percentages of total transferrin. Table 2 also includes the trisialo transferrin percentage content taken on its own (3 sTr).

The first group, the non-drinkers (ND), was of 12 individuals who denied having any alcohol intake. The second group of 26 individuals were social drinkers (SD). 24 individuals having an intake of >60 g alcohol on a regular daily basis were placed in the third group, the alcoholics (A).

TABLE 2

Detected ranges (R) and mean values (M) for 0–2 sTrf, 0–3 sTrf and 3 sTrf expressed as percentages of total transferrin

| Group | 0–2 sTrf R | 0–2 sTrf M | 0–3 sTrf R | 0–3 sTrf M | 3 sTrf R | 3 sTrf M |
|---|---|---|---|---|---|---|
| ND | 0.2–1.8 | 0.98 (0.50) | 2.6–6.7 | 4.69 (1.16) | 2.4–4.9 | 3.71 (0.73) |
| SD | 0.4–2.7 | 1.42 (0.54) | 2.7–9.3 | 5.98 (1.54) | 3.1–7.2 | 4.56 (1.20) |
| A | 1.4–27.6 | 9.98 (7.13) | 10.1–35.6 | 17.89 (7.36) | 3.3–11.6 | 7.9 (1.92) |
| Overlap ND/SD | Yes | | Yes | | Yes | |
| Overlap SD/A | Yes | | No | | Yes | |
| Overlap ND/A | Yes | | No | | Yes | |

The values in brackets are the standard deviations.

EXAMPLE 7

Alternative Assay Kit

Equipment

Columns (5 mm diameter containing 0.5 ml POROS HQ50 (Perseptive Biosystems) covered with a nylon top filter)

Pipettes covering volumes from 4 μl to 3 ml Alternatively: multipipettes for volumes 100 μl, 200 μl, 2 ml and 3 ml Racks (for tubes (75×12 mm)

Microtiter plates

Reader for microtiter plates, 405 nm filter

Reagents

Solution 1
  10 mM BisTris (bis(2-hydroxyethyl)amino-tris-(hydroxymethyl)methane)
  3.1 mM Sodium Azide
  0.05% Tween 20
  1M HCl ad pH 7.0
  0.4 mM Tris base (Tris(hydroxymethyl)aminomethane)
  0.075 mM $FeCl_3$
  0.075 mM Sodium Citrate
  0.2 mM Maleic acid
  deionized $H_2O$ q.s.

Solution 2
  50 mM BisTris (bis(2-hydroxyethyl)amino-tris-(hydroxymethyl)methane)
  3.1 mM Sodium Azide
  0.05% Tween 20
  1M HCl ad pH 6.00
  approx 5 mM NaCl added
  deionized $H_2O$ q.s.

Human Normal Serum

For calibration containing
  2.17 mg/ml Transferrin

Turbidimetric Reagent

900 µl 0.1M PEG-PBS pH 8.2

100 µl Rabbit anti-serum transferrin (Dako)

The 0.1M PEG-PBS pH 8.2 Comprises 91.8 mM Disodiumhydrogenphosphate 8.3 mM Sodiumdihydrogenphosphate *$2H_2O$ 3.1 mM Polyethylene glycol 3.1 mM Sodium Azide 2M NaOH ad pH 8.2 deionized $H_2O$ q.s.

EXAMPLE 8

Preparation of Calibrators and Columns

Prepare 4 calibrators using human normal serum. See table 3 for dilutions

TABLE 3

Preparation of calibrators:

| Calibrators (mg/ml) | Human normal serum containing 2.17 mg transferrin/ml | Solution 2 |
|---|---|---|
| C1:0.002 | 100 µl C3 | 900.0 µl |
| C2:0.01 | 4.6 µl | 995.4 µl |
| C3:0.02 | 10.1 µl | 1089.9 µl |
| C4:0.03 | 13.8 µl | 98.2 µl |

(Calibrator C1 is produced by dilution of calibrator C3 with Solution 2).

Preparation of Columns

Use one column for each sample to be tested. Elute surplus transport buffer by removing first the top and thereafter the bottom stopper, discard and eluate. Prepared columns should be used within 2 hours.

EXAMPLE 9

Sample Testing Procedure

Sample Procedure

1. Add 100 µl serum to 500 µl solution 1 in a test tube. Mix.
2. Incubate for 5–10 minutes at ambient temperature.

Column Separation

1. All solutions added must elute freely from the column.
2. Add 500 µl incubated sample to a column.
3. Let the sample sink into the top filter before adding 1.0 ml of solution 2.
4. Let solution 2 sink into the top filter. Change tubes below columns. Solution eluted up to this point should be discarded. Add 2.0 ml of solution 2 to each column. Collect 2 ml eluate 2.

Measurement

1. Add 200 µl of each calibrator, and 200 µl of eluate 2 from the column separation to separate wells of a microtiter plate. Read at 405 nm.
2. Add 100 µl turbidimetric reagent to each well.
3. Incubate for 15 minutes at ambient temperature.
4. Read results using a reader with 405 nm filter and subtract the background calculated in step 1.
5. Establish a calibration curve using non-linear regression. FIG. 1 shows a typical calibration curve.
6. CDT in the serum sample is calculated from the calibration curve.

EXAMPLE 10

Figure 3:
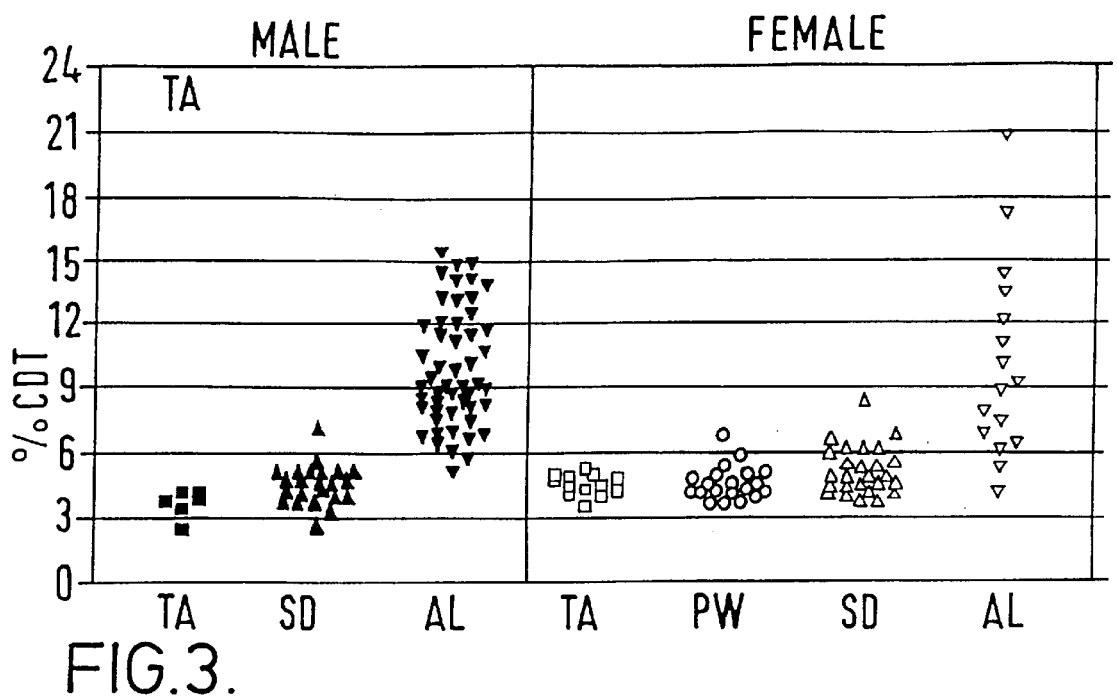
Figure 6:
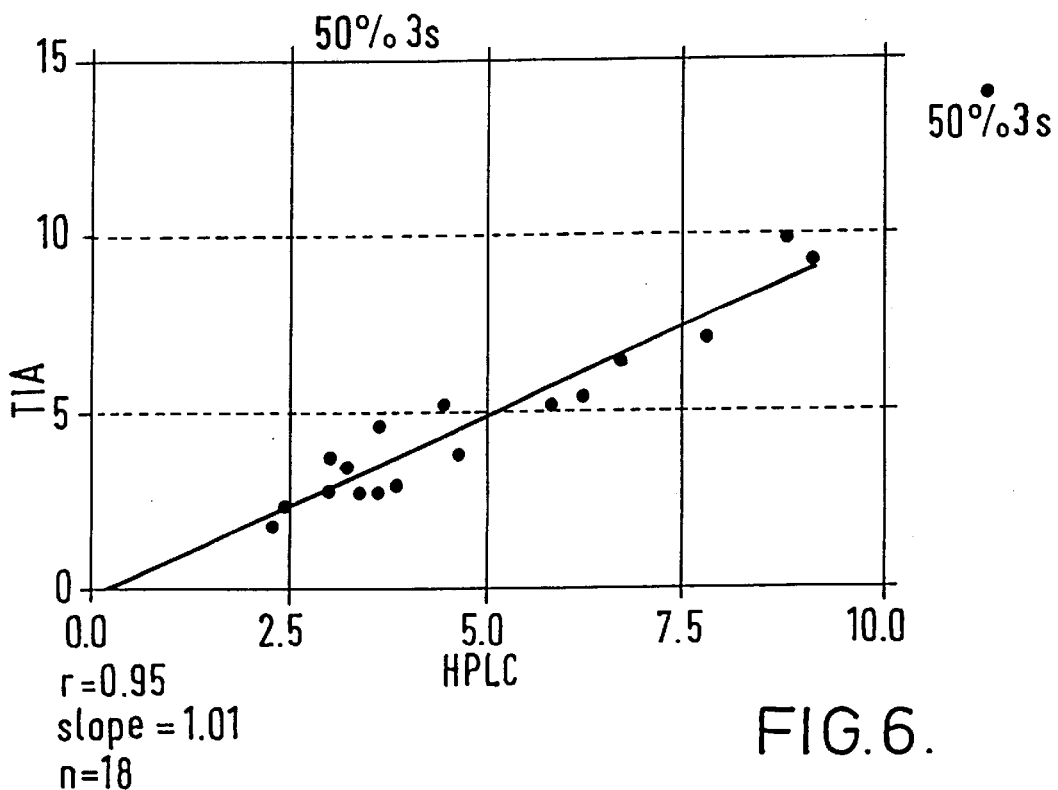
FIG. 6 is a graphical comparison of results for 18 samples tested according to the invention with asialo, monosialo, disialo and 50% trisialo variants being assessed and similarly being tested and assessed by HPLC.

Serum samples from total abstainers (TA), healthy social drinkers (SD) (alcohol consumption below 60 grams/day) and heavy drinkers (AL) (alcohol consumption above 60 g/day) were tested using the method of Example 9. The results, which express asialo, mono-sialo, disialo and 50% of trisialo transferrins as a percentage of CDT, are set out in FIG. 3. These results correlate well with results obtained by HPLC (see FIG. 6) and differentiate well between social and heavy drinkers. There is also a slight difference in % CDT shown between total abstainers and social drinkers. The PW category was for pregnant women where false positives are often found with all methods.

In general a reference limit of 6% CDT for males is found effective for discriminating alcohol abuse.

EXAMPLE 11

HPLC Separation

Serum samples were from 17 alcoholics admitted to hospital due to their heavy drinking habits, and all were drinking close up to the time of admittance. Furthermore, serum was sampled from 25 healthy individuals with moderate alcohol consumption habits (<60 grams per day on an average basis) (social drinkers). Furthermore, serum samples of 9 total abstainers were collected.

120 µl serum samples are pre-treated with 24 µl Fe(III) maleic-citrate (9.25 mM) solution for iron saturation. Thereafter 1.3 µl solution of 100 mg dextran/ml water and 16 µl solution of $CaCl_2$ 147 mg/ml water were added per 120 µl serum.

The samples were kept in a refrigerator for 1 hour before they were centrifuged and 100 µl of supernatant was diluted to 2.15 ml with water before 2.0 ml was applied to a POROS HQ10 (Perseptive Inc, USA) column (0.5 cm×5 cm) for chromatography.

The transferrin variants were eluted by using a $Cl^-$-gradient in a 20 mM Bis-Tris pH=6.1 buffer system. The 450 nm absorption signal from the different variants of transferrin was recorded and the relative amount of each variant was calculated by peak integration.

The clinical information for each sample was correlated to the relative amount of the sum of a-, mono-, and di-sialo-transferrin (% CDT).

Figure 4:
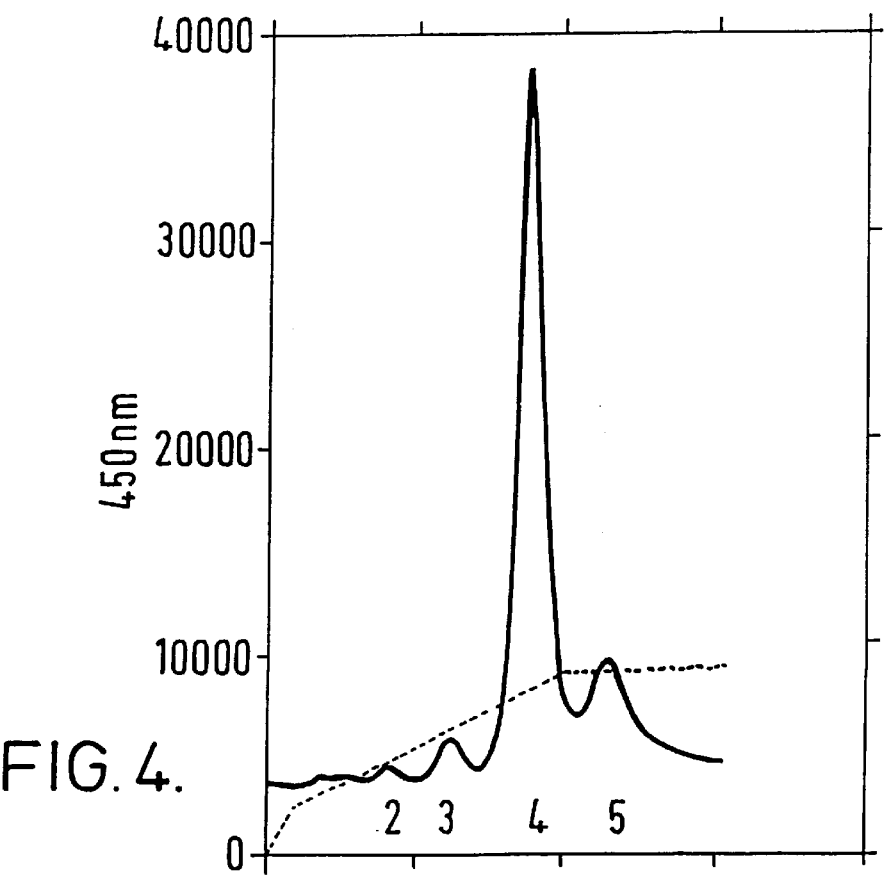
FIG. 4 is an HPLC chromatogram measured at 450 nm and showing peaks for the disialo, trisialo, tetrasialo and pentasialo variants.

FIG. 4 shows the eluting pattern from the HPLC column at 450 nm. The dotted line is the $Cl^-$ gradient. Due to differences in charges the low sialic-acid containing transferrin variants are eluted first. Increasing $Cl^-$-gradient elutes higher sialic-acid containing transferrin molecules.

Figure 5:
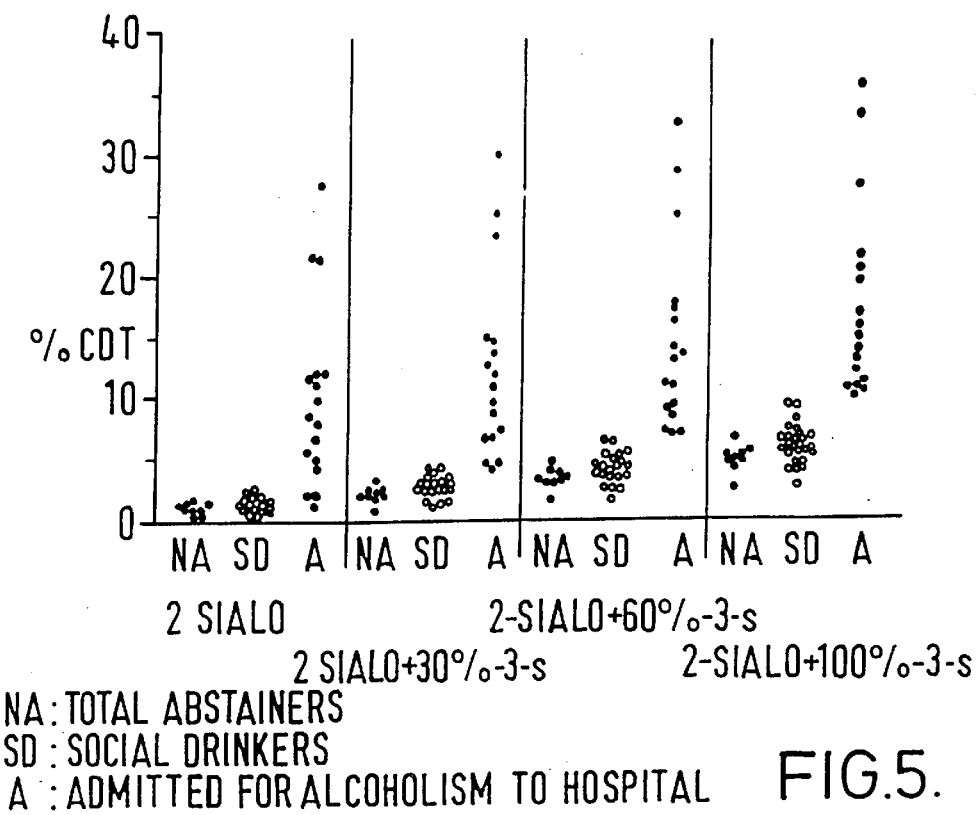

After integration and quantitation of the relative transferrin content of the different fractions of transferrins, values from HPLC chromatograms were calculated as % CDT, including different relative amounts of the 3-sialotransferrin fractions in this value (30%, 50% and 100%). FIG. 5 demonstrates the effect of including different fractions of the 3-sialo-transferrin fraction into the % CDT value, in correlation to the drinking habit subgroups. A clearer separation between the non-drinkers and the alcoholics was achieved when the 3-sialo-transferrin fraction was included, giving better sensitivity and specificity of the assay.

EXAMPLE 12

Best Mode

Alternative Assay Kit

Equipment

Columns (7 mm internal diameter) containing 0.5 ml POROS HQ50 (Perseptive Biosystems) between polyethylene upper and lower porous frits (Porex, Atlanta, Ga., USA)—columns available from Pierce Company, USA Four calibrators prepared as in Example 8

Pipettes covering volumes from 4 μl to 3 ml Alternatively: multipipettes for volumes 100 μl, 200 μl, 2 ml and 3 ml Racks (for tubes (75×12 mm)

Microtiter plates

Reader for microtiter plates, 405 nm filter

Reagents

Solution 1
10 mM BisTris (bis(2-hydroxyethyl)amino-tris-(hydroxymethyl)methane)
3.1 mM Sodium Azide
0.05% Tween 20
1M HCl ad pH 7.0
0.8 mM Tris base (Tris(hydroxymethyl)aminomethane)
0.15 mM $FeCl_3$
0.15 mM Sodium Citrate
0.4 mM Maleic acid
deionized $H_2O$ q.s.

Solution 2
50 mM BisTris (bis(2-hydroxyethyl)amino-tris-(hydroxymethyl)methane)
3.1 mM Sodium Azide
0.05% Tween 20
1M HCl ad pH 6.00
approx 5 mM NaCl added
deionized $H_2O$ q.s.

Turbidimetric Reagent

900 μl 0.3M Tris/PEG pH 7.4
100 μl Rabbit anti-serum transferrin (Dako)

The 0.3M Tris/PEG pH 7.4 Comprises
0.3 m Tris. HCl
6% Polyethylene glycol (PEG 8000)
3.1 mM Sodium Azide
2M NaOH ad pH 7.4
deionized $H_2O$ q.s.

Figure 7:
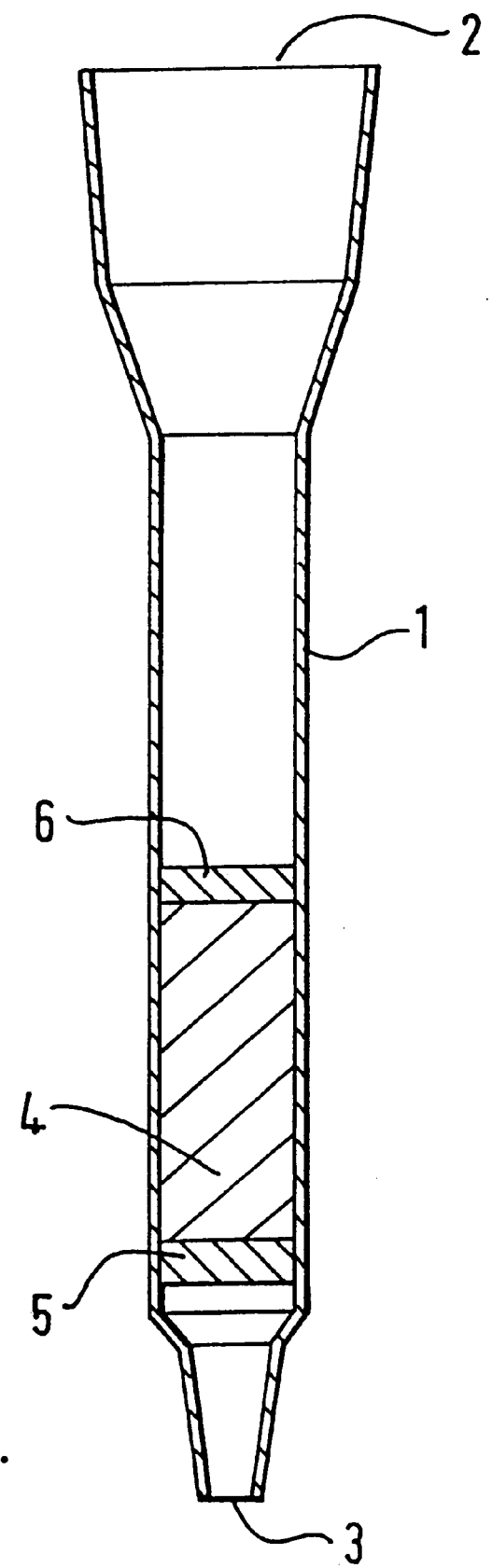
FIG. 7 is a schematic cross-sectional view of a minicolumn usable in the methods of the invention.

Referring to FIG. 7 there is shown a 7 mm internal diameter column 1 with sample introduction and eluate removal ports 2 and 3 containing 1.24 cm resin 4 disposed between porous frits 5 and 6.

Preparation of Columns

Use one column for each sample to be tested. Elute surplus transport buffer by removing first the top and thereafter the bottom stopper, discard and eluate. Prepared columns should be used within 2 hours.

Sample Testing Procedure

Sample Procedure
1. Add 100 μl serum to 500 μl solution 1 in a test tube. Mix.
2. Incubate for 5–10 minutes at ambient temperature.

Column Separation
1. All solutions added must elute freely from the column.
2. Add 500 μl incubated sample to a column.
3. Let the sample sink into the top filter before adding 1.0 ml of solution 2.
4. Let solution 2 sink into the top filter. Change tubes below columns. Solution eluted up to this point should be discarded. Add 2.0 ml of solution 2 to each column. Collect 2 ml eluate 2.

Measurement
1. Add 200 μl of each calibrator, and 200 μl of eluate 2 from the column separation to separate wells of a microtiter plate. Read at 405 nm.
2. Add 100 μl turbidimetric reagent to each well.
3. Incubate for 15 minutes at ambient temperature.
4. Read results using a reader with 405 nm filter and subtract the background calculated in step 1.
5. Establish a calibration curve using non-linear regression. FIG. 1 shows a typical calibration curve.
6. CDT in the serum sample is calculated from the calibration curve.

% CDT Determination
1. Take 50 μL from the incubated sample from "sample procedure" above and add to 2 mL of solution 2.
2. Take 200 μL of the resulting mixture and add to a well of the microtiter plate and measure as in steps 1 to 6 of "measurement" above to give a total transferrin (TT) value.
3. % CDT is calculated as [9.76(CDT/TT)−1.73] where CDT and TT are the measured values for CDT and TT respectively.

EXAMPLE 13

Serum samples from social drinkers (SD) and heavy drinkers (AL) were tested using the method and apparatus of Example 12 and by way of comparison HPLC and the prior art Speciality IEF system (an isoelectric focussing/laser densiometry method).

HPLC Analysis was as Follows

Instrumentation

Analytical HPLC separations were performed using a standard FPLC system from Pharmacia Biotech (Uppsla, Sweden).

The monitoring wavelength on the UV-M detector was 450 nm at a full-scale sensitivity of 0.001 Å with a 5 mm pathlength flowcell with mercury optics. A Pharmacia HR 5/5 column (50 mm×5 mm i.d.) was high-flow packed (7–9 ml/min) with 10 μm particles of Poros HQ 10 (Perseptive Biosystems) to a final gel height of 60 mm.

The column was operated at ambient temperature (20–25° C.).

Data/peak evaluations were performed with a Nelson datamodule. Each chromatogram was base-line integrated by a manual method.

Reagents

Analytical-reagent grade chemicals were used. Aqueous solutions were prepared with ultrapure water from a Milli-Q system (Millipore, Mitford Mass.). All buffer/solutions were filtered through a 0.22 μm (pore size) filter and degassed by ultrasonication before use.

$FeCl_3$ 6 $H_2O$, NaCl, tri-sodium citrate dihydrate, HCl (Titrisol, 1N) and MeOH were purchased from Merck (Darmstadt, F.R.G.). Dextran sulfate and bis-tris were purchased from Fluka (Buchs, Switzerland). Trizma-base, maleic acid and $CaCl_2$ were purchased from Sigma (St. Louis, Mo.).

Sample Preparation

Serum aliquots were stored for less than three months at −20° C. before analysis.

150 μl aliquots of serum thawed at room temperature were briefly vortex-mixed with 30 μl of a 9.25 mM FeCl$_3$-tris-maleic acid solution before capping of the tubes and incubation for 30 minutes at room temperature (20–25° C.). After incubation, 1.6 μl (100 g/l) dextran sulfate and without delay 7.5 μl CaCl$_2$ (147 g/l) were added to the serum samples as lipoprotein precipitation mediators.

The samples were refrigerated for 1 hour at 4–6° C. before removal of the precipitated lipoproteins by centrifugation (5000×g, 15 min.) at 4–6° C.

130 μl of the clear supernates were poured off and diluted 19.5-fold with water and after a 10 minute delay filtered by a syringe filter (0.22 μm pore size) before injection onto a chromatographic column.

The prepared samples could be stored at 4–6° C. overnight before analysis without any detectable alteration of CDT-content.

Chromatographic Conditions

The isoforms of transferrin were separated in a two-buffer system with a multi-step salt gradient elution.

Mobile phase A was 20 mM bis-tris buffer, pH 6.20. Mobile phase B was composed of 20 mM bis-tris buffer, pH 5.60 containing 17.5 g/L, NaCl (300 mM). There was strict control of buffer pH versus temperature.

Regeneration/cleaning solution C consisted of methanol and 1N hydrochloric acid (50/50, by vol.). Separation was performed with a flow rate of 2.0 ml/min with a gradient profile as shown in Table 5.

Injection of 2 ml sample was found to be optimal with relation to eluant dilution, resolution and signal intensity. With the manual regeneration/cleaning procedure shown in Table 6 it was possible to analyse 100 patients samples before the column back pressure exceeded 4 Mpa. At this point an enzymatic treatment of the column was done according to the instructions of the manufacturer.

TABLE 5

| Time (minutes) | Buffer A, % (by vol.) | Buffer B, % (by vol.) |
| --- | --- | --- |
| 0.00 | 100 | 0 |
| 5.00 | 100 | 0 |
| 14.06 | 92 | 8 |
| 18.06 | 92 | 8 |
| 21.09 | 90 | 10 |
| 24.09 | 90 | 10 |
| 26.09 | 86 | 14 |
| 32.09 | 86 | 14 |
| 33.09 | 81.5 | 18.5 |
| 45.00 | 81.5 | 18.5 |

TABLE 6

| Buffer A flow | C-injection volume | Run volume |
| --- | --- | --- |
| 1.0 ml/min | 2.0 ml | 4 ml, bypass flowcell |
| 1.0 ml/min | 2.0 ml | 4 ml, through flowcell |
| 4.0 ml/min | — | 4 ml, through flowcell |
| 3.0 ml/min | — | 10 ml, through flowcell |
| 2.0 ml/min | Injection of sample | Waste 3 ml, start prog. |

The comparative results are set out in Table 7 below.

TABLE 7

| | | | HPLC | | |
| --- | --- | --- | --- | --- | --- |
| Sample ID | Specialty's IEF* | Example 13 % CDT++ | % 0–2S | % 3S | % 0–2S + ½ 3S++ |
| SD16 | 3 | 3.2 | 1.26 | 5.18 | 3.8 |
| SD24 | 4 | 2.2 | 1.62 | 3.99 | 3.6 |
| SD43 | 6 | 4.3 | 1.54 | 5.40 | 4.2 |
| SD44 | 3 | 1.9 | 1.71 | 3.51 | 3.5 |
| SD45 | 2 | 2.9 | 1.46 | 4.70 | 3.8 |
| SD46 | 1 | 3.1 | 1.38 | 4.50 | 3.6 |
| SD47 | 12 | 3.4 | 1.93 | 4.38 | 4.1 |
| SD48 | 3 | 3.8 | 1.45 | 4.38 | 3.6 |
| SD49 | 5 | 3.5 | 1.30 | 3.96 | 3.3 |
| SD50 | 4 | 3.3 | 1.39 | 5.18 | 4.0 |
| SD68 | 5 | 3.9 | 1.51 | 5.07 | 4.0 |
| SD69 | 22 | 6.4 | 2.94 | 4.69 | 5.3 |
| SD70 | 3 | 3.5 | 1.26 | 4.69 | 3.6 |
| SD71 | 3 | 3.8 | 1.34 | 5.96 | 4.3 |
| SD72 | 6 | 4.1 | 1.48 | 4.76 | 3.9 |
| SD73 | 8 | 3.8 | 1.97 | 6.19 | 5.1 |
| SD74 | 4 | 3.1 | 1.47 | 3.40 | 3.2 |
| SD75 | 5 | 2.4 | 1.82 | 4.04 | 3.8 |
| SD76 | 4 | 3.7 | 1.60 | 4.55 | 3.9 |
| SD77 | 3 | 4.7 | 1.63 | 7.91 | 5.6 |
| AL3 | 5 | 3.7 | 2.15 | 2.71 | 3.5 |
| AL5 | 9 | 6.5 | | | |
| AL11 | 8 | 4.6 | 2.19 | 4.13 | 4.3 |
| AL15 | 15 | 7.2 | 2.76 | 6.86 | 6.2 |
| AL30 | 5 | 8.4 | | | |
| AL31 | 13 | 7.8 | 5.30 | 3.82 | 7.2 |
| AL36 | 6 | 6.7 | 5.03 | 2.92 | 6.5 |
| AL0060 | 45 | 14.0 | 10.24 | 9.01 | 14.8 |
| AL0061 | 44 | 14.0 | 10.69 | 8.62 | 15.0 |
| AL0073 | 45 | 13.8 | 10.53 | 5.86 | 13.5 |
| AL0082 | 2 | 6.7 | 3.67 | 6.16 | 6.8 |
| AL0083 | 33 | 8.1 | 5.24 | 4.18 | 7.3 |
| AL0084 | 56 | 17.9 | 14.67 | 5.14 | 17.2 |
| AL0085 | 52 | 18.2 | 14.45 | 4.91 | 16.9 |
| AL0088 | 32 | | 10.83 | 5.80 | 13.7 |
| AL0119 | 33 | 10.8 | 7.81 | 3.23 | 9.4 |
| AL0120 | 32 | 13.1 | 9.68 | 3.14 | 11.3 |

*Threshold value 8
++Threshold value 6%

EXAMPLE 14

Preparation of Loaded Columns for Assay Kits

POROS HQ 50 gel is obtained from Perseptive Biosystems Inc., USA in 2L containers containing a transport buffer and 1L gel. The transport buffer is removed by suction and a wash buffer (10L made up from Bis Tris 41.8 g, sodium azide 2.0 g, sodium chloride 584.4 g, Tween 20 5.0 g and water, pH adjusted to 7.0±0.1 with HCl) is added to the container to suspend the gel. The gel from several containers is transferred to a 100L mixing container and further wash buffer is added to a total of 1L/L gel. The mixture is stirred with a mixer, 15 min in each direction, and allowed to sediment overnight. The wash buffer is then removed by suction. 1L/L gel of a second wash buffer (10L made up from Bis Tris 41.8 g, sodium azide 2.0 g, Tween 20 5.0 g and water, pH adjusted to 7.0±0.05 with HCl) is added and the mixture is again stirred 15 min in each direction and allowed to sediment overnight. The wash buffer is then removed by suction and washed three times with 1L/L gel of a transport buffer (10L made up from Bis-Tris 104.6 g, sodium azide 2.0 g, Tween 20 5.0 g and water, pH adjusted to 7.0±0.03 with HCl), being stirred 15 min in each direction, allowed to sediment overnight and having the buffer removed by suction as above. The gel is then resuspended 19.9% v/v in the transport buffer. Gel prepared in this way may be used in the kits and assays described in the earlier Examples. Thus for example 2.7 mL volumes may be loaded into 7 mm internal diameter columns as shown in FIG. 7 (from Pierce Company, USA) between polyethylene upper and lower porous frits (Porex, Atlanta, Ga., USA) and these loaded columns may be used in the kit of Example 12.

I claim:

1. A method of assessment of carbohydrate-deficient transferrin in a transferrin containing body fluid, said method comprising the steps of:

i) obtaining a transferrin containing liquid sample of or derived from a said fluid;

ii) contacting said sample with a source of iron ions;

iii) subsequently contacting said sample with an anionic ion exchange resin at a pH such as to cause carbohydrate-deficient transferrin to be retained by said resin;

iv) subsequently contacting said resin with an eluant serving to release carbohydrate-deficient transferrin into the eluate from said resin;

v) collecting a volume of said eluate substantially free from tetra- and penta-sialo transferrin; and vi) assessing the transferrin content in said volume of eluate turbidimetrically or nephelometrically.

2. A method as claimed in claim 1 wherein in step iv) said resin is contacted with an amount of said eluant predetermined to be sufficient only to release from said resin an eluate substantially free of tetra- and penta-sialo transferrin.

3. A method as claimed in claim 2 wherein said amount of said eluant is predetermined to be sufficient to release 30 to 70% of the trisialo transferrin releasable from said resin by said eluant.

4. A method as claimed in claim 2 wherein said amount of said eluant is predetermined to be sufficient to release 40 to 60% of the trisialo transferrin releasable from said resin by said eluant.

5. A method as claimed in claim 1 wherein said body fluid is blood.

6. A method as claimed in claim 5 wherein said liquid sample is serum or plasma.

7. A method as claimed in claim 1 wherein in step ii) said liquid sample is contacted with an aqueous Fe (III) solution.

8. A method as claimed in claim 7 wherein between steps ii) and iii) there is a time interval of 2 to 30 minutes.

9. A method as claimed in claim 1 wherein the pH of said resin with which said sample is contacted is in the range 6.8 to 7.5.

10. A method as claimed in claim 1 wherein said resin is a tertiary or quaternary amine resin.

11. A method as claimed in claim 1 wherein said eluant has a pH of between 5.5 and 6.5.

12. A method as claimed in claim 11 wherein opacity in said eluate is generated by contacting said eluate with an anti-transferrin antibody of antibody fragment.

13. A method as claimed in claim 12 wherein a polymeric opacification enhancer is added to said eluate.

14. A method as claimed in claim 13 wherein between addition of said antibody of antibody fragment and of said enhancer to said eluate and determination of transferrin variant content there is a time interval of 5 to 60 minutes.

15. A method as claimed in claim 1 wherein light of wavelength about 405 nm or about 340 nm is used in the determination of transferrin content.

16. A method as claimed in claim 1 wherein in step vi) a transferrin content of at least 1 mg/L in said eluate is assessed turbidimetrically.

17. A method as claimed in claim 1 wherein the total transferrin content of said sample is also assessed and the carbohydrate deficient transferrin content is determined as a percentage of the total transferrin content.

18. A kit for a diagnostic assay for carbohydrate deficient transferrin according claim 1, said kit comprising:

and iron ion containing buffered incubation solution having a pH of at least 6.2;

optionally, a transferrin solution of known concentration;

an anionic ion exchange resin packed in a container having sample introduction and eluate removal ports;

optionally, a flushing eluant having a pH and ionic strength insufficient to release transferrin from said resin;

a release eluant having a pH and ionic strength sufficient to release transferrin from said resin;

optionally, a light transmitting eluate receiving vessel;

optionally, an anti-transferrin antibody or antibody fragment; and optionally, an opacification enhancer.

19. A kit as claimed in claim 18 containing said incubation solution, said resin, said flushing eluant and said release eluant.

20. A kit as claimed in claim 18 wherein disposed adjacent said resin at the sample introduction port end thereof is a porous filter element serving in practice to prevent air entry into said resin following introduction through said introduction port of sample of eluant.

21. A method of assaying for alcohol consumption, said method comprising obtaining a first transferrin containing liquid sample of or derived from a body fluid and containing tetra- and pent-sialo transferrins;

obtaining from said first sample a second transferrin containing liquid sample, said second sample containing asialo, monoasialo and disialo variants, and being substantially free from tetra- and penta-sialo transferrin and having a transferrin content of at least 1 mg/L; and turbidimetrically or nephelometrically assessing the transferrin content of said second sample.

22. A method as claimed in claim 21 wherein the content of desialo transferrin in said second fluid sample is assessed as the proportion the total transferrin content in said sample provided by the asialo, monosialo, disialo and 40 to 60% of the trisialo transferrin variants.

23. The method according to claim 21 wherein the second sample also contains trisialo-transferrin.

* * * * *